United States Patent [19]

Pangburn

[11] Patent Number: 5,361,786
[45] Date of Patent: Nov. 8, 1994

[54] NAIL TREATMENT METHOD

[76] Inventor: William E. Pangburn, 12171 Loma Rica Dr., Grass Valley, Calif. 95945

[21] Appl. No.: 96,224

[22] Filed: Jul. 26, 1993

[51] Int. Cl.$^5$ .............................................. A45D 24/00
[52] U.S. Cl. ..................................... 132/200; 132/76.4
[58] Field of Search ................. 132/200, 76.4, 76.5; 51/293, 295, 309

[56] References Cited

U.S. PATENT DOCUMENTS

| | | | |
|---|---|---|---|
| 2,308,624 | 1/1943 | Pouech | 132/76.4 |
| 2,699,791 | 1/1955 | Hansen | 132/76.4 |
| 3,762,895 | 10/1973 | Keeleric | 51/293 |
| 4,407,310 | 10/1983 | Jadow | 132/73 |
| 4,459,987 | 7/1984 | Pangburn . | |
| 4,497,694 | 2/1985 | Bankier et al. | 132/76.4 |
| 4,534,138 | 8/1985 | Pangburn . | |
| 4,572,222 | 2/1986 | Pangburn . | |
| 4,621,465 | 11/1986 | Pangburn . | |
| 4,712,552 | 12/1987 | Pangburn . | |
| 4,844,885 | 7/1989 | Chernack | 424/61 |
| 4,930,529 | 6/1990 | Whitney | 132/76.5 |

Primary Examiner—Gene Mancene
Assistant Examiner—Frank A. LaViola
Attorney, Agent, or Firm—William W. Haefliger

[57] ABSTRACT

The method of reforming fingernail or toenail surface that includes providing an undulating multi-beadlike glass surface on a substrate; and reciprocating the glass surface against the nail surface while applying pressure thereto via the substrate and the glass surface, thereby to reform the nail surface.

9 Claims, 2 Drawing Sheets

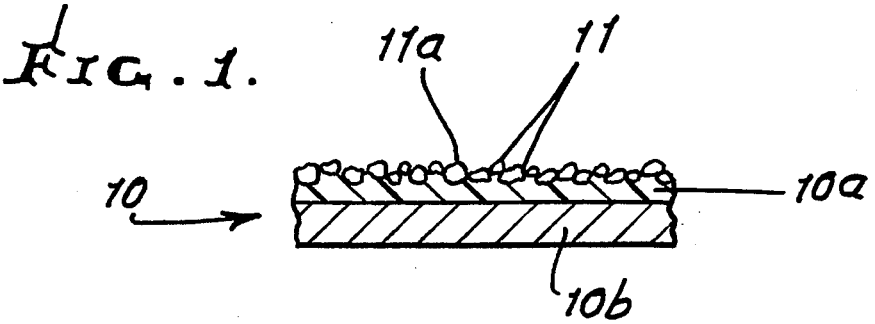
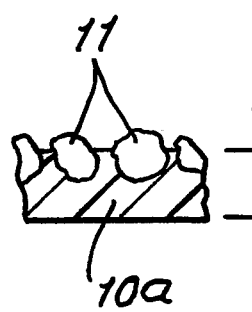
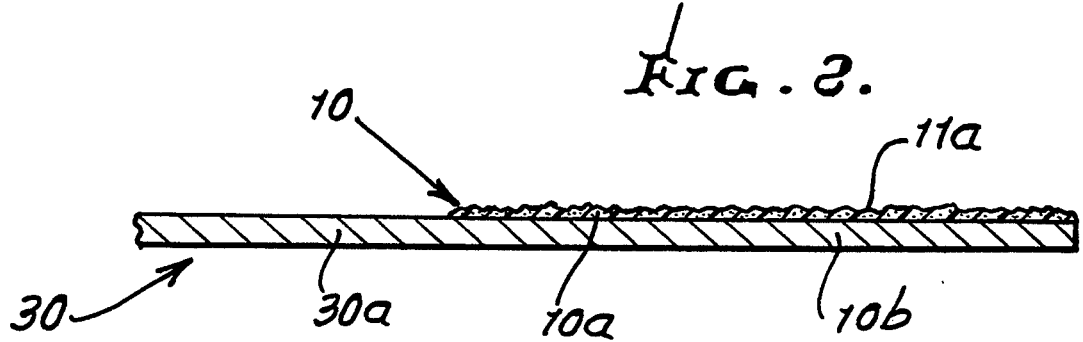
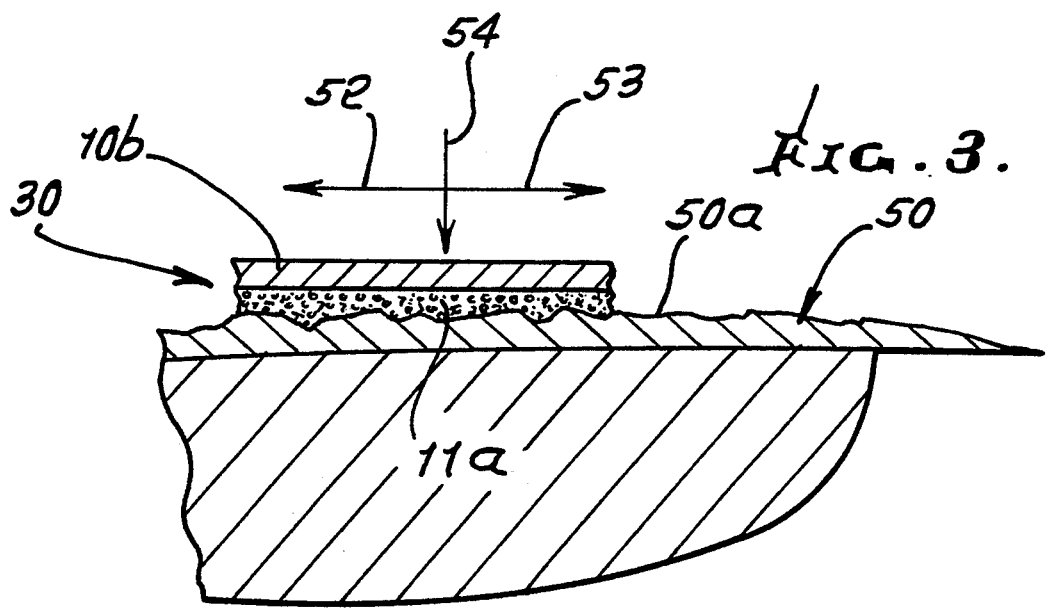

NAIL TREATMENT METHOD

BACKGROUND OF THE INVENTION

This invention relates generally to fingernail or toenail treatment, and more particularly concerns reforming nail surfaces to enable enhanced gripping of nail coatings to nail surfaces.

Nail coatings such as nail polishes tend to peel and fragment after undesirably short time intervals following their application to nail surfaces. So called "base coats" have been applied to nail surfaces in an effort to prolong the useful lives of polishes applied over such base coats; however they too tend to peel and break-off too soon after application. There is need for method and means to enhance attachment of nail coatings to nail surfaces so as to significantly prolong the useful lives of such coatings.

SUMMARY OF THE INVENTION

It is a major object of the invention to provide method and apparatus meeting the above need.

Basically the method of the invention has to do with reforming a fingernail or toenail surface in order to enhance attachment of the nail coating, such as a "base coat", for example; and the method includes the steps:
 a) providing an undulating multi-beadlike glass surface on a substrate,
 b) and reciprocating the surface against the nail surface while applying pressure thereto via the substrate and the glass surface, thereby to reform the nail surface.

As will be seen, the method may be carried out by attaching multiple glass beads of very small size to the substrate to form the nail surface reforming means. Also, the reciprocation step may be carried out to cause the beads to travel successively over and to depress nail surface plateaus or protrusions, thereby to form plateau edges. A flowable nail coating may then be applied to the nail surface to contact such edges for locking to same upon curing of the coating. The edges may, for example, be created as overhang edges due to the glass bead reforming action.

The device itself for thus reforming a fingernail or toenail surface typically comprises:
 a) an elongated substrate,
 b) and an undulating glassy surface on the elongated substrate,
 c) whereby the undulating glassy surface may be reciprocated against the nail surface while applying pressure thereto via the substrate and the glassy surface, thereby to reform the nail surface.

As referred to above, the device undulating glassy surface may advantageously comprise an areal succession of glass beads adherent to the substrate.

Yet another object is to provide method and apparatus for reducing the roughness of plastic surfaces other than nail surfaces.

These and other objects and advantages of the invention, as well as the details of an illustrative embodiment, will be more fully understood from the following specification and drawings, in which:

DRAWING DESCRIPTION

FIG. 1 is a fragmentary section taken through a device incorporating the invention;

FIG. 1a is an enlarged fragmentary view showing glass bead retention by the substrate;

FIG. 2 is a view showing the FIG. 1 device in the form of a hand manipulable "file like" tool;

FIG. 3 is an enlarged section showing a fingernail surface being reformed by the FIG. 2 device;

DETAILED DESCRIPTION

Figure 4:
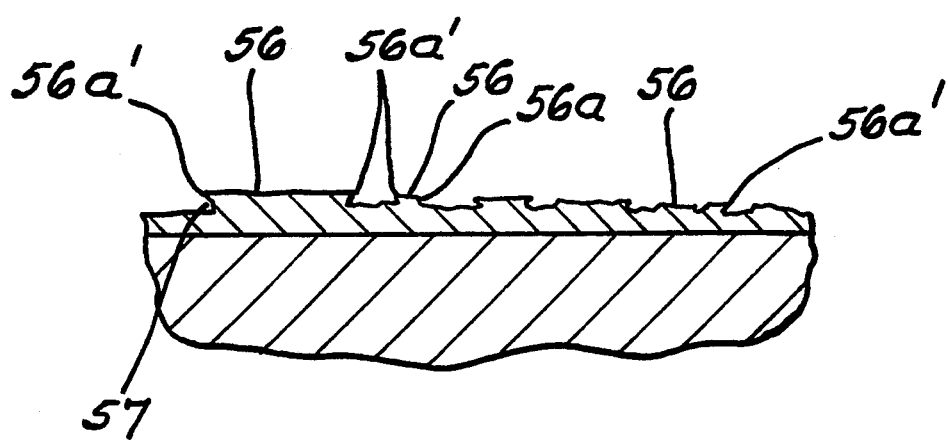
Fig.4 is an enlarged section showing the reformed nail surface, wherein edges have been formed on flattened protrusions.

In FIGS. 1 and 2 an elongated substrate 10 is provided. An undulating glassy surface 11a is provided on the substrate, and may advantageously be formed by an areal succession of glass beads 11 adherent to the substrate. The beads may extend in a layer as shown; and FIG. 1a shows horizontally positioned beads 11 partly embedded or anchored in and bonded to the substrate material 10a, the beads protruding from that material or pad to be employed as described herein. That substrate material may advantageously consist of pourable silicone polymer or adhesive sealant as for example General Electric RTV 108 which vulcanizes at room temperature. It contains a suitable curing agent. Also usable is GE RTV 118 which is self leveling when poured on a surface. RTV 108 and 118 are both translucent, tough and durable. Beads 11 are then dispensed to cover the upper side of the silicone layer prior to complete curing. The particles become bonded to and/or partly embedded in the silicone, and as the latter cures, the acetoxy or other curing agent vaporizes. The resultant sheet or pad has generally uniform thickness, and may be cut to shape. After about 15 to 20 minutes from time of pour, the silicone layer or sheet is cured, at room temperature.

One usable silicone formulation is known as dimethyl polysiloxane, and the curing agent is acetic anhydride.

The glass beads are sized between 5 and 400 microns, as determined by passage through a Taylor screen or screens.

FIGS. 1 and 2 also show the substrate as including a nail file like solid material as for example molded plastic material extending in a sheet 10b as shown. The sheet 10b may form a nail file like support for the substrate material 10c, referred to, the substrate portion 10a bonded to the substrate portion 10b.

The thickness "t" of the substrate material 10a may be between 0.015 and 0.100 inches.

The method of using the formed device 30 is shown in FIG. 3. A fingernail or toenail is shown at 50, and has an upwardly presented undulating surface shown at 50a. The device 30 is inverted so that the glassy undulating surface 11a is presented downwardly to engage the nail surface 50a. Undulations on the latter have crest to crest lengths typically much longer than the crest to crest lengths on successive glass beads presented downwardly. Surface 11a is then reciprocated (see arrows 52 and 53) against the nail surface while pressure is applied via 10b, in direction 54, thereby to reform the nail surface.

Figure 5:
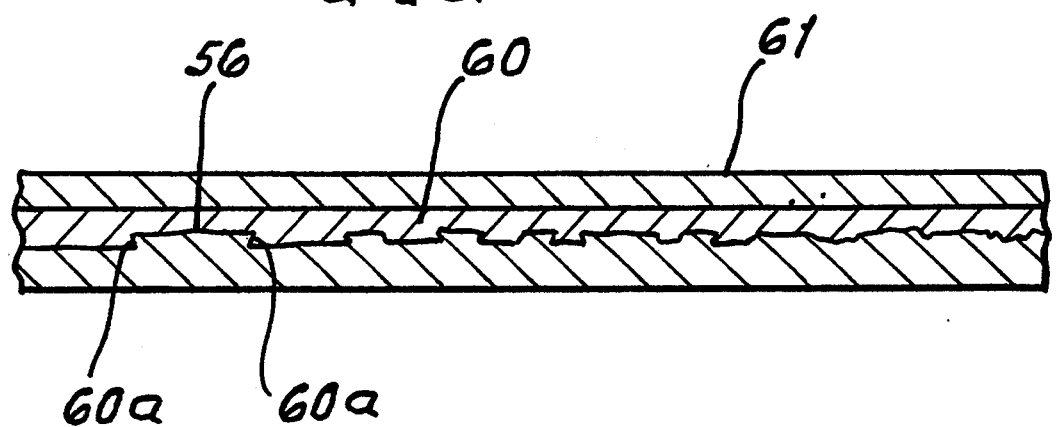
FIG. 5 is a view like FIG. 4, showing base-coat locking to the reformed nail surface, and a polish coating on the base-coat.

FIG. 4 shows the reformed nail surface as including permanently depressed plateaus 56 having laterally presented edges 56a. Such edges may be characterized as including overhang edges 56a', i.e. overhanging locking spaces 57 beneath the overhang edges, in the manner of dovetail configuration. Subsequently, and as seen in FIG. 5, when flowable nail coating material 60 is applied to and over the plateaus, and cured, that coat adheres by locking to the plateaus and the edges as by flowing into overhang spaces 57 at 60a to cure therein and lock thereto.

Coating 60 may comprise a pre-coat to which nail polish 61 is subsequently applied in a flowable layer, to cure thereon.

The article or device 30 is shown in FIG. 2 as having a handle 30a that may be grasped for reciprocation and pressure application as described in connection with FIG. 3.

The described method and apparatus may be carried out and employed with respect to plastic work surfaces other than nail surfaces, as for example to reduce surface roughness, and without application of a coating material over the flattened plateau areas. FIGS. 1–4 may be considered as representing such a work surface, as at 50a, to be smoothed or otherwise having its roughness reduced.

I claim:

1. The method of reforming fingernail or toenail surface that includes the steps:
   a) providing an undulating multi-bead exclusively glass surface on a substrate,
   b) and reciprocating said glass surface against a nail surface while applying pressure thereto via the substrate and the glass surface, thereby to reform said nail surface.

2. The method of claim 1 including attaching multiple glass beads to said substrate to form said undulating surface.

3. The method of claim 2 wherein said glass beads are sized between 5 micron and 400 microns.

4. The method of claim 1 wherein said step b) is carried out to depress nail surface plateaus thereby to form plateau edges.

5. The method of claim 4 including applying a flowable nail coating layer to said nail surface, to contact said edges, and curing said coating layer for locking the coating to said edges.

6. The method of claim 5 including applying nail polish to said coating.

7. The method of claim 4 wherein said edges are formed as overhang edges.

8. The method of treating a fingernail or toenail, that includes
   a) permanently depressing nail plateaus, to form plateau edges, by providing a multi-bead exclusively glass surface on a substrate and reciprocating said glass surface on said nail plateaus,
   b) applying a flowable coating to the nail surface to contact said edges,
   c) and allowing said coating to cure to lock to said edges, whereby the coating is firmly attached to the nail at its depressed surface.

9. The method of claim 8 wherein said edges are formed as overhang edges.

* * * * *